United States Patent [19]

Uhr et al.

[11] Patent Number: 5,096,903

[45] Date of Patent: Mar. 17, 1992

[54] FUNGICIDAL TRISUBSTITUTED 1,2,4-TRIAZINE-3,5-DIONES

[75] Inventors: Hermann Uhr, Leverkusen; Arno Widdig, Odenthal; Dieter Berg, Wuppertal; Gerd Hänssler, Leverkusen, all of Fed. Rep. of Germany

[73] Assignee: Bayer Aktiengesellschaft, Leverkusen, Fed. Rep. of Germany

[21] Appl. No.: 644,049

[22] Filed: Jan. 18, 1991

[30] Foreign Application Priority Data

Jan. 26, 1990 [DE] Fed. Rep. of Germany ....... 4002297

[51] Int. Cl.$^5$ ................ C07D 253/075; A01N 43/707
[52] U.S. Cl. ..................................... 514/242; 544/182
[58] Field of Search ........................ 544/182; 514/242

[56] References Cited

U.S. PATENT DOCUMENTS 4,631,278 12/1986 Boeck .................................. 544/182

FOREIGN PATENT DOCUMENTS 3618662 12/1987 Fed. Rep. of Germany .
WO86/00072 1/1986 PCT Int'l Appl. .

OTHER PUBLICATIONS

J. Med. Chem. 1981, 24, 1337–1342, Max W. Willer, Anticoccidial Derivatives of 6-Azauracil.
Pharmaceuticals, pp. 1–2, 84479V/49, Substd. 2--phenyl-as-triazine-3,5(2H, 4H) diones.

*Primary Examiner*—John M. Ford
*Attorney, Agent, or Firm*—Sprung Horn Kramer & Woods

[57] ABSTRACT

Fungicidal trisubstituted 1,2,4-triazine-3,5-diones of the formula

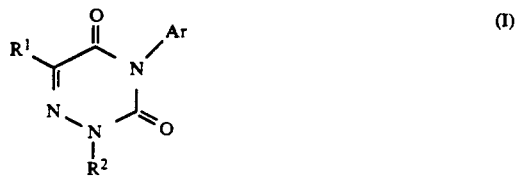

in which
Ar represents optionally substituted aryl,
$R^1$ represents an optionally substituted aliphatic of cycloaliphatic radical and
$R^2$ represents an optionally substituted aliphatic radical.

Many of the intermediates therefor where $R^2$ is hydrogen and/or the 3-O is replaced by 3-S are also new.

11 Claims, No Drawings

FUNGICIDAL TRISUBSTITUTED 1,2,4-TRIAZINE-3,5-DIONES

The invention relates to new trisubstituted 1,2,4-triazine-3,5-diones, to processes for their preparation and to their use for pest-combating, above all as fungicides, and to new intermediates.

It has already been disclosed that 2-phenyl-1,2,4-triazine-3,5-diones are suitable as selective herbicides (WO 8600-072-A).

In addition, various 1-aryl-6-azaurazils are known which are suitable for combating coccidiosis (for example Miller, Max. W. et al., J. Med. Chem., 24, 1337 (1981); BE 815-246; US 4631-278-A).

It has additionally been disclosed that 6-azathymine is suitable as an additional component in tumour treatment with 5-fluorouracil (J 55-111,420).

Until now, no 1,2,4-triazine-3,5-diones were known which were suitable as fungicides.

In addition, it has already been disclosed that structurally similar trisubstituted 1,3,5-triazine-2,4,6-triones (compare DE-OS (German Published Specification) 3,618,662) have a fungicidal action.

However, the activity of these compounds is not completely satisfactory in all areas of application, in particular at low application rates and concentrations.

New trisubstituted 1,2,4-triazine-3,5-diones of the general formula (I)

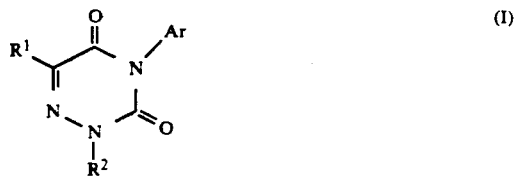

in which
Ar represents optionally substituted aryl,
R¹ represents an optionally substituted aliphatic or cycloaliphatic radical and
R² represents an optionally substituted aliphatic radical, have now been found.

It has furthermore been found that the new trisubstituted 1,2,4-triazine-3,5-diones of the general formula (I)

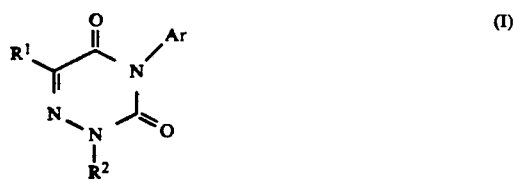

in which
Ar represents optionally substituted aryl,
R¹ represents an optionally substituted aliphatic or cycloaliphatic radical and
R² represents an optionally substituted aliphatic radical, are obtained when the disubstituted 1,2,4-triazine-3,5-diones, some of which are also new, of the general formula (II)

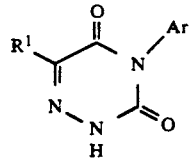

where Ar and R¹ have the abovementioned meanings, are reacted with compounds of the general formula (III)

$$R^2-X \qquad (III)$$

in which
R² has the abovementioned meaning and
X denotes a leaving group, such as, for example, halogen, sulphate, mesylate or tosylate,
if appropriate in the presence of a diluent and if appropriate in the presence of an acid-binding agent.

Finally, it has been found that the new trisubstituted 1,2,4-triazine-3,5-diones of the formula (I) have very good biological properties and are suitable, above all, for the selective combating of harmful fungi, in particular in rice.

Formula (I) provides a general definition of the trisubstituted 1,2,4-triazine-3,5-diones according to the invention. Preferred compounds of the formula (I) are those in which Ar represents phenyl which is optionally monosubstituted to pentasubstituted by identical or different substituents from the series comprising halogen, alkyl having 1 to 10 carbon atoms, alkenyl having 2 to 10 carbon atoms, alkynyl having 2 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino with straight-chain or branched alkyl radicals having 1 to 6 carbon atoms, dialkylamino with identical or different, straight-chain or branched alkyl radicals each having 1 to 6 carbon atoms, cycloalkyl or cycloalkenyl having 3 to 8 carbon atoms which are optionally monosubstituted to hexasubstituted by identical or different substituents from the series comprising halogen, alkyl having 1 to 4 carbon atoms, alkoxy having 1 to 4 carbon atoms, halogenoalkyl having 1 to 4 carbon atoms or halogenoalkoxy having 1 to 4 carbon atoms and in each case 1 to 9 identical or different halogen atoms, alkylthio having 1 to 4 carbon atoms and halogenoalkylthio having 1 to 4 carbon atoms and 1 to 5 identical or different halogen atoms, R¹ represents straight-chain or branched alkyl having 1 to 12 carbon atoms, straight-chain or branched alkenyl having 3 to 12 carbon atoms or straight-chain or branched alkynyl having 3 to 12 carbon atoms, which are optionally monosubstituted to polysubstituted by identical or different substituents from the series comprising halogen, alkoxy having 1 to 4 carbon atoms, halogenoalkoxy having 1 to 4 carbon atoms and 1 to 9 identical or different halogen atoms, alkylthio having 1 to 4 carbon atoms and halogenoalkylthio having 1 to 4 carbon atoms and 1 to 9 identical or different halogen atoms; or $R^1$ represents cycloalkyl having 3 to 8 carbon atoms, which is optionally monosubstituted to hexasubstituted by identical or different substituents from the series comprising halogen, alkyl having 1 to 4 carbon atoms, alkoxy having 1 to 4 carbon atoms, halogenoalkyl or halogenoalkoxy having 1 to 4 carbon atoms and 1 to 9 identical or different halogen atoms, alkylthio having 1 to 4 carbon atoms and halogenoalkylthio having 1 to 4 carbon atoms and 1 to 9 identical or different halogen atoms, $R^2$ represents alkyl having 1 to 10 carbon atoms, alkenyl having 3 to 10 carbon atoms, alkynyl having 3 to 10 carbon atoms, alkoxyalkyl in each case having 1 to 4 carbon atoms in the alkoxy and in the alkyl moiety, alkylthioalkyl in each case having 1 to 4 carbon atoms in the alkylthio moiety and in the alkyl moiety, alkoxycarbonylalkyl having 1 to 4 carbon atoms in the alkoxy moiety and 1 to 3 carbon atoms in the alkyl moiety or represents cyanoalkyl having 1 to 5 carbon atoms in the alkyl moiety.

Compounds of the formula (I) to be particularly emphasized are those in which

Ar represents phenyl which may optionally be monosubstituted to tetrasubstituted by identical or different substituents from the series comprising fluorine, chlorine, bromine, alkyl having 1 to 9 carbon atoms, alkenyl having 2 to 9 carbon atoms, alkynyl having 2 to 9 carbon atoms, halogenoalkyl having 1 to 7 carbon atoms and 1 to 7 chlorine and/or fluorine atoms, alkoxy having 1 to 9 carbon atoms, halogenoalkoxy having 1 to 7 carbon atoms and 1 to 7 chlorine and/or fluorine atoms, alkylthio having 1 to 9 carbon atoms, halogenoalkylthio having 1 to 7 carbon atoms and 1 to 7 chlorine and/or fluorine atoms, amino, monoalkylamino with a straight-chain or branched alkyl radical having 1 to 5 carbon atoms, dialkylamino with identical or different, straight-chain or branched alkyl radicals each having 1 to 5 carbon atoms, cycloalkyl or cycloalkenyl having 3 to 7 carbon atoms which is optionally monosubstituted to pentasubstituted by identical or different substituents from the series comprising chlorine and/or fluorine, alkyl having 1 to 3 carbon atoms, alkoxy having 1 to 3 carbon atoms, halogenoalkoxy having 1 to 3 carbon atoms and 1 to 5 chlorine and/or fluorine atoms, alkylthio having 1 to 3 carbon atoms and halogenoalkylthio having 1 to 3 carbon atoms and 1 to 5 chlorine and/or fluorine atoms, $R^1$ represents straight-chain or branched alkyl having 1 to 10 carbon atoms, straight-chain or branched alkenyl having 3 to 10 carbon atoms, or straight-chain or branched alkynyl having 3 to 10 carbon atoms, which are in each case optionally monosubstituted to trisubstituted by identical or different substituents from the series comprising chlorine and/or fluorine, alkoxy having 1 to 3 carbon atoms, halogenoalkoxy having 1 to 3 carbon atoms and 1 to 3 chlorine and/or fluorine atoms, alkylthio having 1 to 3 carbon atoms, and halogenoalkylthio having 1 to 3 carbon atoms and 1 to 3 chlorine and/or fluorine atoms; or $R^1$ furthermore represents cycloalkyl having 3 to 7 carbon atoms, which is optionally monosubstituted to hexasubstituted by identical or different substituents from the series comprising fluorine, chlorine, alkyl having 1 to 3 carbon atoms, alkoxy having 1 to 3 carbon atoms, halogenoalkoxy having 1 to 3 carbon atoms and 1 to 3 chlorine and/or fluorine atoms, alkylthio having 1 to 3 carbon atoms and halogenoalkylthio having 1 to 3 carbon atoms and 1 to 3 chlorine and/or fluorine atoms, $R^2$ represents alkyl having 1 to 9 carbon atoms, alkenyl having 3 to 9 carbon atoms, alkynyl having 3 to 9 carbon atoms, alkoxyalkyl having 1 or 2 carbon atoms in the alkoxy moiety and 1 to 3 carbon atoms in the alkyl moiety, alkylthioalkyl having 1 or 2 carbon atoms in the alkylthio moiety and 1 to 3 carbon atoms in the alkyl moiety, alkoxycarbonylalkyl having 1 or 2 carbon atoms in the alkoxy moiety and 2 or 3 carbon atoms in the alkyl moiety, or cyanoalkyl having 1 to 3 carbon atoms in the alkyl moiety.

Compounds of the formula (I) which are to be very particularly emphasized are those in which Ar represents phenyl which may optionally be monosubstituted to trisubstituted by identical or different substituents from the series comprising fluorine, chlorine, bromine, alkyl having 1 to 8 carbon atoms, alkenyl having 2 to 8 carbon atoms, alkynyl having 2 to 8 carbon atoms, halogenoalkyl having 1 to 6 carbon atoms and 1 to 5 chlorine and/or fluorine atoms, alkoxy having 1 to 8 carbon atoms, halogenoalkoxy having 1 to 6 carbon atoms and 1 to 5 chlorine and/or fluorine atoms, alkylthio having 1 to 8 carbon atoms, halogenoalkylthio having 1 to 6 carbon atoms and 1 to 5 chlorine and/or fluorine atoms, amino, monoalkylamino with a straight-chain or branched alkyl radical having 1 to 4 carbon atoms, dialkylamino with identical or different, straight-chain or branched alkyl radicals each having 1 to 4 carbon atoms, cycloalkyl or cycloalkenyl having 3 to 6 carbon atoms, which are optionally monosubstituted to tetrasubstituted by identical or different substituents from the series comprising chlorine, fluorine, alkyl having 1 to 3 carbon atoms, alkoxy having 1 to 3 carbon atoms, halogenoalkoxy having 1 or 2 carbon atoms and 1 to 5 chlorine and/or fluorine atoms, alkylthio having 1 or 2 carbon atoms and halogenoalkylthio having 1 or 2 carbon atoms and 1 to 5 chlorine and/or fluorine atoms, $R^1$ represents straight-chain or branched alkyl having 1 to 9 carbon atoms, straight-chain or branched alkenyl having 3 to 9 carbon atoms or straight-chain or branched alkinyl having 3 to 9 carbon atoms, which in each case are optionally monosubstituted or disubstituted by identical or different substituents from the series comprising chlorine, fluorine, alkoxy having 1 to 3 carbon atoms, halogenoalkoxy having 1 to 3 carbon atoms and 1 to 3 chlorine and/or fluorine atoms, alkylthio having 1 to 3 carbon atoms, and halogenoalkylthio having 1 to 3 carbon atoms and 1 to 3 chlorine and/or fluorine atoms; or $R^1$ furthermore represents cycloalkyl having 3 to 7 carbon atoms, which is optionally monosubstituted to pentasubstituted by identical or different substituents from the series comprising fluorine, chlorine, alkyl having 1 or 2 carbon atoms, alkoxy having 1 or 2 carbon atoms, halogenoalkoxy having 1 or 2 carbon atoms and 1 to 4 chlorine and/or fluorine atoms, alkylthio having 1 or 2 carbon atoms and halogenoalkylthio having 1 or 2 carbon atoms and 1 to 3 chlorine and/or fluorine atoms, $R^2$ represents alkyl having 1 to 8 carbon atoms, alkenyl having 3 to 8 carbon atoms, alkynyl having 3 to 8 carbon atoms, alkoxyalkyl having 1 or 2 carbon atoms in the alkoxy moiety and 1 to 3 carbon atoms in the alkyl moiety, alkylthioalkyl having 1 or 2 carbon atoms in the alkylthio moiety and 1 to 3 carbon atoms in the alkyl moiety, alkoxycarbonylalkyl having 1 or 2 carbon atoms in the alkoxy moiety and 2 or 3 carbon atoms in the alkyl moiety or cyanoalkyl having 1 to 3 carbon atoms in the alkyl moiety.

If, for example, 4-phenyl-6-tert.-butyl-1,2,4-triazine-3,5-dione and ethyl iodide are used as starting materials according to the process according to the invention, the course of the reaction can be described by the following equation:

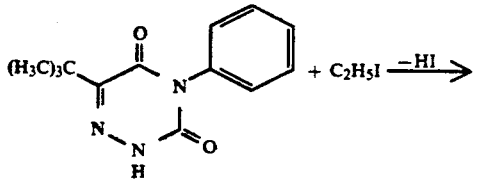

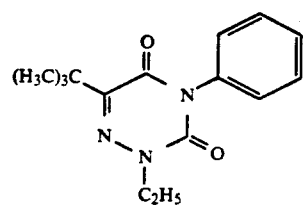

The reaction temperatures can be varied within a large temperature range in this process. In general, the reaction is carried out between 20° C. and 150° C., preferably between 50° C. and 120° C.

When carrying out the process, the starting materials and, if desired, the acid-binding agent are employed in approximately equimolar amounts. An excess of acid-binding agents is in general not harmful.

The reactions are preferably carried out in the presence of a diluent Suitable diluents are all inert organic solvents. These preferably include hydrocarbons such as toluene and xylene; chlorinated hydrocarbons such as chlorobenzene and chloroform; ketones such as acetone, ethers such as tetrahydrofuran and dioxane; and nitriles such as acetonitrile.

Acid-binders used can be all customary acid-binding agents. These preferably include tertiary amines such as triethylamine and pyridine; alkali metal hydroxides such as sodium hydroxide and potassium hydroxide and alkali metal carbonates and hydrogencarbonates such as potassium carbonate and sodium hydrogencarbonate.

The compounds according to the invention are worked up and isolated in a customary manner. They are either immediately obtained in crystalline form or remain as a crystallizate or oil after evaporating the solvent.

The alkylating agents of the formula (III) required as starting compounds in the process according to the invention are known. Preferably, in this case X represents chloride, bromide, iodide, tosylate or sulphate. $R^2$ preferably has that meaning which has already been mentioned in connection with the description of the substances of the formula (I) according to the invention.

Formula (II) provides a general definition of the 1,2,4-triazine-3,5-diones furthermore required as starting compounds.

The compounds of the formula (IIa)

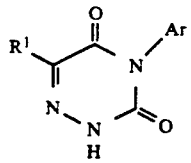

in which
Ar represents optionally substituted aryl and
$R^1$ represents an optionally substituted aliphatic or cycloaliphatic radical,
excluding the compounds in which Ar represents phenyl or 4-methylphenyl and $R^1$ simultaneously represents methyl, are new and likewise a part of the invention.

The new and known compounds of the formula (II)

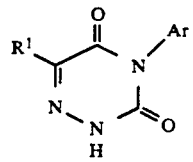

in which
Ar represents optionally substituted aryl,
$R^1$ represents an optionally substituted aliphatic or cycloaliphatic radical,
are obtained when 3-thioxo-1,2,4-triazin-5-ones of the general formula (IV)

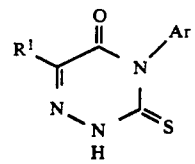

in which Ar and $R^1$ have the abovementioned meanings, are reacted with desulphurization reagents, if appropriate in the presence of a diluent.

The preferred, particularly preferred and very particularly preferred definitions of the substituents $R^1$ and Ar in the formulae (II) and (IIa) correspond to those which were given in the formula (I).

If, for example, 4-phenyl-6-tert.-butyl-3-thioxo-1,2,4-triazin-5-one is reacted with $H_2O_2/KOH$ as the desulphurization reagent, the course of the reaction for the preparation of the compounds of the formula (II) can be described by the following equation:

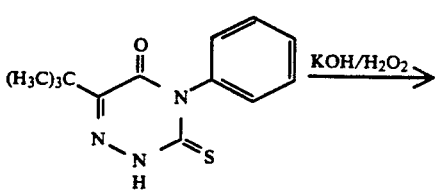

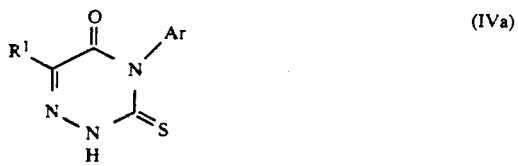

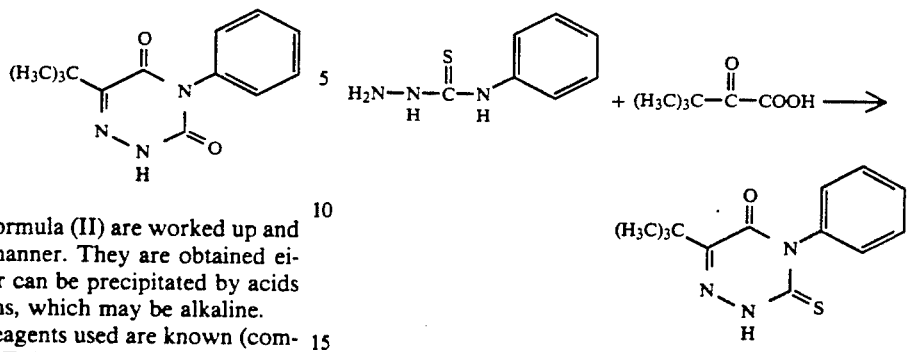

The substances of the formula (II) are worked up and isolated in a customary manner. They are obtained either in crystalline form or can be precipitated by acids from the reaction solutions, which may be alkaline.

The desulphurization reagents used are known (compare H. Neunhoeffer, P. F. Wiley; The Chemistry of Heterocyclic compounds; Chemistry of 1,2,3-Triazines and 1,2,4-Triazines, Tetrazines and Pentazines; Wiley-Interscience, N.Y. 1978, p. 266 and M. Tisler et. al., J. Org. Chem. 25, 770 (1960)). Accordingly, $H_2O_2$ in the presence of KOH or NaOH; NaOBr, $KMnO_4$, $I_2$/NaOH or chloroacetic acid are used, inter alia.

Formula (IV) provides a general definition of the 3-thioxo-1,2,4-triazin-5-ones to be used for the preparation of compounds of the formula (II). The compounds of the formula (IVa)

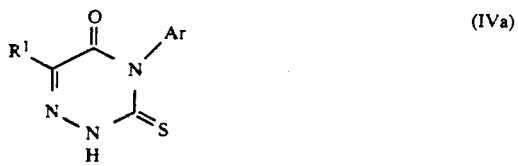

in which

Ar represents optionally substituted aryl and $R^1$ represents an optionally substituted aliphatic or cycloaliphatic radical, excluding the compounds in which Ar represents phenyl, 4-methylphenyl, 3-methylphenyl, 2-methoxyphenyl, 3-methoxyphenyl, 2-ethoxyphenyl or 4-chlorophenyl and $R^1$ simultaneously represents methyl, are new and a part of the invention.

The new and known 3-thioxo-1,2,4-triazin-5-ones of the formula (IV), in which Ar and $R^1$ have the abovementioned meaning, are prepared by reacting α-ketocarboxylic acids of the general formula (V)

where $R^1$ has the abovementioned meaning, with thiosemicarbazides of the general formula (VI)

where Ar has the abovementioned meaning, if appropriate in the presence of a diluent and if appropriate in the presence of an acid (M. Tisler et. al., J. Org. Chem. 25, 770 (1960)).

If, for example, 4-phenylthiosemicarbazide and 2-keto-3,3-dimethylbutyric acid are employed as starting materials according to this process, the course of the reaction can be described by the following equation:

The α-ketocarboxylic acids required are known. $R^1$ preferably has that meaning which has already been mentioned in connection with the description of the substances of the general formula (II) and (IV) and the active compounds of the general formula (I) according to the invention. The 4-aryl-thiosemicarbazides of the general formula (VI) are known per se and can be obtained in a known manner from aromatic thioisocyanates and hydrazine. Ar preferably has that meaning which has already been mentioned in connection with the description of the substances of the general formula (II) and (IV) and the active compounds of the general formula (I) according to the invention.

The reaction temperatures can be varied within a large temperature range in the process. In general, the reaction is carried out between 20° C. and 150° C., preferably between 40° C. and 120° C. When carrying out the reaction, the starting materials are employed in equimolar amounts. The α-ketocarboxylic acids can also be generated from their corresponding alkali metal salts by adding acid.

The reactions are preferably carried out in the presence of a diluent. Suitable diluents are organic solvents, water or mixtures of these. Hydrocarbons such as toluene or xylene, chlorinated hydrocarbons such as chlorobenzene or chloroform, ketones such as acetone, ethers such as tetrahydrofuran and dioxane, nitriles such as acetonitrile and alcohols such as ethanol or methanol are preferably used.

Acids which can be used are all customary inorganic and organic acids. These preferably include hydrochloric acid, sulphuric acid, phosphoric acid, formic acid, acetic acid and oxalic acid.

The intermediates of the formula (IV) are worked up and isolated in a customary manner. They are usually obtained in crystalline form or can be recovered from the reaction media by extraction.

The active compounds of the formula (I) according to the invention have a strong biological action and can be employed in practice for combating undesired pests. The active compounds are suitable for use, for example, as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;* Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae:*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can present in the formulations as a mixture with other known active compounds, such as fungicides, insecticides and acaricides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of the soil, active compound concentrations of 0.00001 to 0.1% by weight, preferably of 0.0001 to 0.02% by weight, are required at the place of action.

The compounds according to the invention also show an action against true mildew on cucumbers and vines and, at appropriate concentrations, they show a leaf-insecticidal action.

PREPARATION EXAMPLES (Example 2)

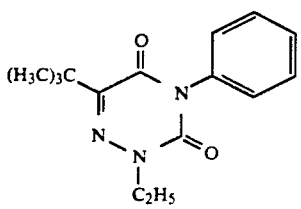

8 g (0.033 mol) of 4-phenyl-6-tert.-butyl-1,2,4-triazine-3,5-dione, 6.2 g (0.040 mol) of ethyl iodide and 9 g of potassium carbonate are boiled under reflux for 12 hours in 100 ml of absolute acetonitrile. After cooling, the solid is filtered off, the filtrate is evaporated and the residue is triturated with hot water. The crystalline reaction product is filtered off with suction and recrystallized from methanol. 8.65 g (96% of theory) of the desired compound are obtained. For physical data see Example 2 in the following table.

The compounds of the formula (I) mentioned in the following table are prepared analogously to the example given or to the methods described in the text:

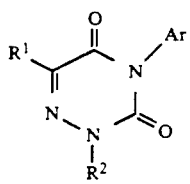

(I)

| Example No. | Ar | $R^1$ | $R^2$ | Physical constants |
|---|---|---|---|---|
| 1 | —⟨⟩—OCF$_3$ | —C(CH$_3$)$_3$ | —C$_2$H$_5$ | M.p. = 96° C. |
| 2 | —⟨⟩ | —C(CH$_3$)$_3$ | —C$_2$H$_5$ | M.p. = 80° C. |
| 3 | —⟨⟩—OCH$_3$ | —C(CH$_3$)$_3$ | —CH$_3$ | IR: 1721, 1665 br* cm$^{-1}$ |
| 4 | —⟨⟩—CH$_3$ | —C(CH$_3$)$_3$ | —C$_2$H$_5$ | M.p. = 120° C. |
| 5 | —⟨⟩—Cl | —C(CH$_3$)$_3$ | —C$_2$H$_5$ | M.p. = 146° C |
| 6 | —⟨⟩—OC$_2$H$_5$ | —C(CH$_3$)$_3$ | —CH$_3$ | IR: 1719, 1670 br* cm$^{-1}$ |

-continued
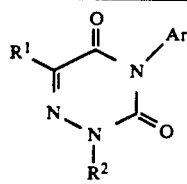
(I)
| Example No. | Ar | $R^1$ | $R^2$ | Physical constants |
|---|---|---|---|---|
| 7 | 2-Cl-phenyl | $-C(CH_3)_3$ | $-CH_3$ | M.p. = 124° C. |
| 8 | 2-Cl-phenyl | $-C(CH_3)_3$ | $-C_2H_5$ | M.p. = 92° C. |
| 9 | 2-Cl-phenyl | $-C(CH_3)_3$ | $-C_3H_7$ | M.p. = 58° C. |
| 10 | 3,5-(CH$_3$)$_2$-phenyl | $-C(CH_3)_3$ | $-CH_3$ | IR: 1719, 1668 cm$^{-1}$ |
| 11 | 3,5-(CH$_3$)$_2$-phenyl | $-C(CH_3)_3$ | $-C_2H_5$ | M.p. = 126° C. |
| 12 | 3,5-(CH$_3$)$_2$-phenyl | $-C(CH_3)_3$ | $-CH_2-CH=CH_2$ | M.p. = 140° C. |
| 13 | 3,5-(CH$_3$)$_2$-phenyl | $-C(CH_3)_3$ | $-CH_2-C\equiv CH$ | M.p. = 156° C. |
| 14 | 3,5-(CH$_3$)$_2$-phenyl | $-C(CH_3)_3$ | $-CH(CH_3)_2$ | M.p. = 140° C. |

-continued
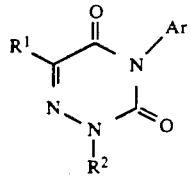
(I)
| Example No. | Ar | R¹ | R² | Physical constants |
|---|---|---|---|---|
| 15 | 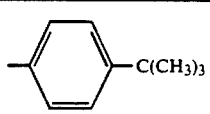 | —C(CH₃)₃ | —CH₃ | M.p. = 156° C. |
| 16 | 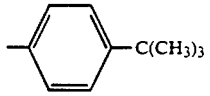 | —C(CH₃)₃ | —C₂H₅ | IR: 1720, 1671 cm⁻¹ |
| 17 | 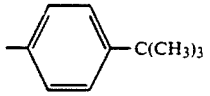 | —C(CH₃)₃ | —CH₂—CH=CH₂ | IR: 1720, 1650-1670 cm⁻¹ |
| 18 | 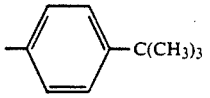 | —C(CH₃)₃ | —C₃H₇ | IR: 1720, 1670 cm⁻¹ |
| 19 | 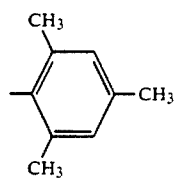 | —C(CH₃)₃ | —CH₃ | M.p. = 178° C. |
| 20 | 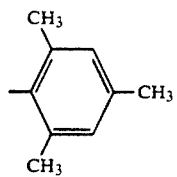 | —C(CH₃)₃ | —C₂H₅ | M.p. = 86° C. |
| 21 | 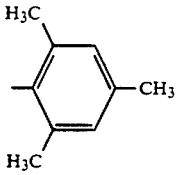 | —C(CH₃)₃ | —C₄H₉ | M.p. = 95° C. |
| 22 | 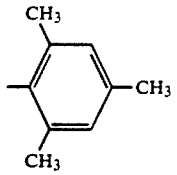 | —C(CH₃)₃ | —C₃H₇ | M.p. = 90° C. |
| 23 | 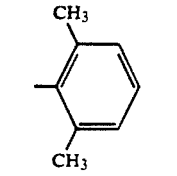 | —C(CH₃)₃ | —C₂H₅ | M.p. = 118° C. |

-continued

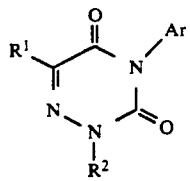
(I)

| Example No. | Ar | R¹ | R² | Physical constants |
|---|---|---|---|---|
| 24 | 2,6-dimethylphenyl (H₃C, H₃C) | $-C(CH_3)_3$ | $-C_4H_9$ | IR: 1719, 1668 cm$^{-1}$ |
| 25 | 2,5-dimethylphenyl (CH₃, CH₃) | $-C(CH_3)_3$ | $-C_2H_5$ | M.p. = 100° C. |
| 26 | 3,4-dimethylphenyl (CH₃, H₃C) | $-C(CH_3)_3$ | $-C_5H_{11}$ | |
| 27 | 3,4-dimethylphenyl (CH₃, H₃C) | $-C(CH_3)_3$ | $-CH_2-C\equiv CH$ | IR: 1722, 1660–1690 cm$^{-1}$ |
| 28 | 4-isopropylphenyl (CH(CH₃)₂) | $-C(CH_3)_3$ | $-CH_3$ | IR: 1718, 1670 cm$^{-1}$ |
| 29 | 4-isopropylphenyl (CH(CH₃)₂) | $-C(CH_3)_3$ | $-C_2H_5$ | IR: 1720, 1670 cm$^{-1}$ |
| 30 | 4-isopropylphenyl (CH(CH₃)₂) | $-C(CH_3)_3$ | $-CH_2-CH=CH_2$ | IR: 1720, 1675 cm$^{-1}$ |
| 31 | 2-methoxyphenyl (OCH₃) | $-C(CH_3)_3$ | $-CH_3$ | M.p. = 126° C. |
| 32 | 2-methoxyphenyl (OCH₃) | $-C(CH_3)_3$ | $-C_2H_5$ | M.p. = 100° C. |

-continued

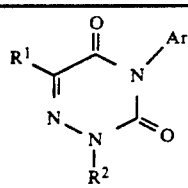

| Example No. | Ar | R¹ | R² | Physical constants |
|---|---|---|---|---|
| 33 | 2,3-dichlorophenyl | —C(CH₃)₃ | —C₂H₅ | M.p. = 92° C. |
| 34 | 2,6-dichlorophenyl | —C(CH₃)₃ | —CH₂—CH=CH₂ | M.p. = 90° C. |
| 35 | 4-N(CH₃)₂-phenyl | —CH(CH₃)₂ | —CH₃ | M.p. = 168° C. |
| 36 | 4-N(CH₃)₂-phenyl | —CH(CH₃)₂ | —CH₂—CH=CH₂ | IR: 1721, 1670, 1608 cm⁻¹ |
| 37 | 4-CH(CH₃)₂-phenyl | —CH(CH₃)₂ | —C₂H₅ | IR: 1720, 1673 cm⁻¹ |
| 38 | 4-CH(CH₃)₂-phenyl | —CH(CH₃)₂ | —CH₂—CH=CH₂ | IR: 1721, 1675, 1600 cm⁻¹ |
| 39 | 4-C(CH₃)₃-phenyl | —CH(CH₃)₂ | —C₂H₅ | IR: 1721, 1670 br*, 1600 cm⁻¹ |
| 40 | 4-C(CH₃)₃-phenyl | —CH(CH₃)₂ | —CH₃ | M.p. = 78° C. |
| 41 | 4-CH(CH₃)₂-phenyl | —CH(CH₃)₂ | —C₃H₇ | IR: 1720, 1675, 1600 cm⁻¹ |
| 42 | 4-C(CH₃)₃-phenyl | —CH(CH₃)₂ | —C₃H₇ | IR: 1720, 1675, 1600 cm⁻¹ |
| 43 | 4-OCF₃-phenyl | —CH(CH₃)₂ | —C₂H₅ | M.p. = 56° C. |

-continued

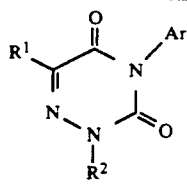
(I)

| Example No. | Ar | R[1] | R[2] | Physical constants |
|---|---|---|---|---|
| 44 | 4-(N(CH$_3$)$_2$)-C$_6$H$_4$- | -CH(CH$_3$)$_2$ | -C$_2$H$_5$ | M.p. = 114° C. |
| 45 | 2,6-Cl$_2$-C$_6$H$_3$- | -C(CH$_3$)$_3$ | -C$_3$H$_7$ | M.p. = 88° C. |
| 46 | 2,6-Cl$_2$-C$_6$H$_3$- | -C(CH$_3$)$_3$ | -CH$_3$ | M.p. = 162° C. |
| 47 | 2,3-Cl$_2$-C$_6$H$_3$- | -C(CH$_3$)$_3$ | -CH$_3$ | M.p. = 136° C. |
| 48 | 4-(OCF$_3$)-C$_6$H$_4$- | -CH(CH$_3$)$_2$ | -CH$_2$-CH=CH$_2$ | M.p. = 48° C. |
| 49 | 4-(C(CH$_3$)$_3$)-C$_6$H$_4$- | -CH(CH$_3$)$_2$ | -CH$_2$-CH=CH$_2$ | IR: 1720, 1665, 1600 cm$^{-1}$ |
| 50 | 4-cyclohexyl-C$_6$H$_4$- | -C(CH$_3$)$_3$ | -CH$_2$-CH=CH$_2$ | IR: 1720, 1670 cm$^{-1}$ |
| 51 | 4-cyclohexyl-C$_6$H$_4$- | -C(CH$_3$)$_3$ | -C$_2$H$_5$ | IR: 1720, 1670 cm$^{-1}$ |
| 52 | 4-cyclohexyl-C$_6$H$_4$- | -C(CH$_3$)$_3$ | -CH$_3$ | M.p. = 114° C. |
| 53 | 4-cyclohexyl-C$_6$H$_4$- | -C(CH$_3$)$_3$ | -C$_3$H$_7$ | M.p. = 118° C. |

-continued

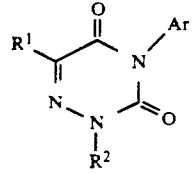
(I)

| Example No. | Ar | R¹ | R² | Physical constants |
|---|---|---|---|---|
| 54 | 4-(CH₂)₅CH₃-C₆H₄- | $-C(CH_3)_3$ | $-CH_3$ | IR: 1720, 1660–1675 cm⁻¹ |
| 55 | 4-(CH₂)₅CH₃-C₆H₄- | $-C(CH_3)_3$ | $-C_2H_5$ | M.p. = 40° C. |
| 56 | 2-H₃CO-C₆H₄- | $-CH(CH_3)_2$ | $-CH_2-C(=O)-OC_2H_5$ | M.p. = 66° C. |
| 57 | 2-H₃CO-C₆H₄- | $-CH(CH_3)_2$ | $-C_2H_5$ | M.p. = 88° C. |
| 58 | 4-CH₃-C₆H₄- | $-CH(CH_3)_2$ | $-CH_3$ | M.p. = 116° C. |
| 59 | 4-CH(CH₃)₂-C₆H₄- | $-C(CH_3)(C_2H_5)_2$ | $-CH_2-CH=CH_2$ | IR: 1720, 1670 cm⁻¹ |
| 60 | 4-CH(CH₃)₂-C₆H₄- | $-C(CH_3)(C_2H_5)_2$ | $-C_2H_5$ | IR: 1721, 1670–1680 cm⁻¹ |
| 61 | 4-cyclohexyl-C₆H₄- | $-CH(CH_3)_2$ | $-CH_2-CH=CH_2$ | IR: 1720, 1675, 1600 cm⁻¹ |
| 62 | 4-CH(CH₃)₂-C₆H₄- | $-C(CH_3)(C_2H_5)_2$ | $-CH_3$ | IR: 1722, 1670 br*, 1580 cm⁻¹ |
| 63 | 4-CH(CH₃)₂-C₆H₄- | $-C(CH_3)(C_2H_5)_2$ | $-C_3H_7$ | IR: 1721, 1670 br*, 1580 cm⁻¹ |
| 64 | 2-Cl-C₆H₄- | $-CH(CH_3)_2$ | $-CH_3$ | M.p. = 74° C. |

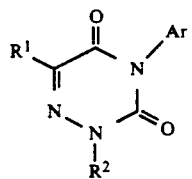

(I)

| Example No. | Ar | R¹ | R² | Physical constants |
|---|---|---|---|---|
| 65 | 2-chlorophenyl | —CH(CH$_3$)$_2$ | —CH(CH$_3$)$_2$ | M.p. = 94° C. |
| 66 | 4-isopropylphenyl | —C(CH$_3$)(C$_2$H$_5$)$_2$ | —C$_4$H$_9$ | IR: 1720, 1670, 1580 cm$^{-1}$ |
| 67 | 4-(3-pentyl)phenyl | —C(CH$_3$)$_3$ | —C$_2$H$_5$ | IR: 1720, 1670, 1580 cm$^{-1}$ |
| 68 | 2,4,6-trimethylphenyl | —CH$_3$ | —CH$_3$ | M.p. = 192° C. |
| 69 | 2,4,6-trimethylphenyl | —CH$_3$ | —C$_4$H$_9$ | M.p. = 90° C. |
| 70 | 4-(3-methylbut-2-yl)phenyl | —C(CH$_3$)$_3$ | —C$_2$H$_5$ | IR: 1720, 1678, 1580 cm$^{-1}$ |
| 71 | 4-(3-pentyl)phenyl | —C(CH$_3$)$_3$ | —CH$_2$—CH=CH$_2$ | IR: 1720, 1670, 1580 cm$^{-1}$ |
| 72 | 4-(3-pentyl)phenyl | —C(CH$_3$)$_3$ | —CH$_3$ | IR: 1720, 1670–1680, br* 1580 cm$^{-1}$ |
| 73 | 4-(3-pentyl)phenyl | —C(CH$_3$)$_3$ | —C$_3$H$_7$ | IR: 1720, 1675, 1580 cm$^{-1}$ |
| 74 | 4-ethoxyphenyl | —CH(CH$_3$)$_2$ | —C$_4$H$_9$ | M.p. = 58° C. |

-continued

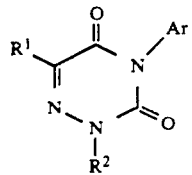
(I)

| Example No. | Ar | R¹ | R² | Physical constants |
|---|---|---|---|---|
| 75 | ―⟨⟩―OC₂H₅ | ―CH(CH₃)₂ | ―CH₂―CH=CH₂ | M.p. = 60° |
| 76 | ―⟨⟩―CH(CH₃)₂ | ―C(CH₃)(C₂H₅)₂ | ―CH₂―C≡CH | IR: 1720, 1670 br*, 1585 cm⁻¹ |
| 77 | ―⟨⟩―C₆H₁₁ | ―CH(CH₃)₂ | ―C₂H₅ | M.p. = 68° C. |
| 78 | ―⟨⟩―CH₃ | ―CH(CH₃)₂ | ―CH₂―C≡CH | M.p. = 108° C. |
| 79 | ―⟨⟩(2-Cl, 4-Cl) | ―C(CH₃)₃ | ―CH₃ | M.p. = 152° C. |
| 80 | ―⟨⟩(3-Cl, 5-Cl) | ―C(CH₃)₃ | ―CH₃ | M.p. = 136° C. |
| 81 | ―⟨⟩―N(CH₃)₂ | ―C(CH₃)₃ | ―C₂H₅ | M.p. = 96° C. |
| 82 | ―⟨⟩―C₃H₇ | ―C(CH₃)₃ | ―CH₃ | IR: 1720, 1675, 1580 cm⁻¹ |
| 83 | ―⟨⟩―C₃H₇ | ―C(CH₃)₃ | ―C₂H₅ | M.p. = 74° C. |
| 84 | ―⟨⟩―C₃H₇ | ―C(CH₃)₃ | ―C₃H₇ | M.p. = 70° C. |
| 85 | ―⟨⟩―C₃H₇ | ―C(CH₃)₃ | ―C₄H₉ | IR: 1720, 1672, 1580 cm⁻¹ |

-continued

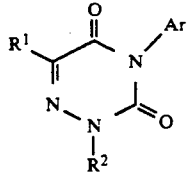
(I)

| Example No. | Ar | R¹ | R² | Physical constants |
|---|---|---|---|---|
| 86 | —⟨⟩—C₃H₇ | —C(CH₃)₃ | —CH₂—CH=CH₂ | M.p. 60° C. |
| 87 | —⟨⟩—C₃H₇ | —C(CH₃)₃ | —CH₂—C≡CH₂ | |
| 88 | —⟨⟩—N(C₂H₅)₂ | —C(CH₃)₃ | —CH₃ | M.p. = 68° C. |
| 89 | —⟨⟩—N(C₂H₅)₂ | —C(CH₃)₃ | —C₂H₅ | M.p. 98° C. |
| 90 | —⟨⟩—N(C₂H₅)₂ | —C(CH₃)₃ | —C₃H₇ | IR: 1722, 1675, 1580 cm⁻¹ |
| 91 | —⟨⟩—N(C₂H₅)₂ | —C(CH₃)₃ | —CH₂—CH=CH₂ | M.p. = 92° C. |
| 92 | —⟨⟩—C(CH₃)₃ | —C(CH₃)(C₂H₅)₂ | —CH₃ | IR: 1720, 1672, 1580 cm⁻¹ |
| 93 | —⟨⟩—N(C₂H₅)₂ | —C(CH₃)₃ | —C₄H₉ | M.p. = 86° C. |
| 94 | —⟨⟩—C(CH₃)₃ | —C(C₂H₅)₂CH₃ | —C₂H₅ | IR: 1718, 1670 cm⁻¹ |
| 95 | —⟨⟩—C(CH₃)₃ | —C(C₂H₅)₂CH₃ | —C₃H₇ | IR: 1720, 1670 cm⁻¹ |
| 96 | —⟨⟩—C(CH₃)₃ | —C(C₂H₅)₂CH₃ | —CH₂CH=CH₂ | IR: 1718, 1675, 1410, 1270 cm⁻¹ |

-continued

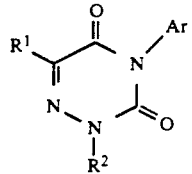
(I)

| Example No. | Ar | $R^1$ | $R^2$ | Physical constants |
|---|---|---|---|---|
| 97 | ![4-C(CH3)3-phenyl] | $-C(C_2H_5)_2CH_3$ | $-C_4H_9$ | IR: 1720, 1675, 1415, 1285 cm$^{-1}$ |
| 98 | ![4-C(CH3)3-phenyl] | $-CH(CH_3)(C_2H_5)$ | $-CH_3$ | IR: 1716, 1670 cm$^{-1}$ |
| 99 | ![4-C(CH3)3-phenyl] | $-CH(CH_3)(C_2H_5)$ | $-C_4H_9$ | IR: 1720, 1670, 1420, 1290 cm$^{-1}$ |
| 100 | ![4-C(CH3)3-phenyl] | $-CH_2-CH(CH_3)_2$ | $-C_2H_5$ | IR: 1720, 1670, 1420, 1295 cm$^{-1}$ |
| 101 | ![4-C(CH3)3-phenyl] | $-CH_2-CH(CH_3)_2$ | $-C_3H_7$ | IR: 1720, 1670, 1422, 1290 cm$^{-1}$ |
| 102 | ![4-C(CH3)3-phenyl] | $-C_3H_7$ | $-C_2H_5$ | IR: 1718, 1660, 1420, 1285 cm$^{-1}$ |
| 103 | ![4-C(CH3)3-phenyl] | $-C_3H_7$ | $-CH(CH_3)_2$ | IR: 1718, 1665, 1420, 1285 cm$^{-1}$ |
| 104 | ![4-C(CH3)3-phenyl] | $-CH(CH_3)(C_2H_5)$ | $-C_2H_5$ | IR: 1710, 1660, 1420, 1290 cm$^{-1}$ |
| 105 | ![4-SC4H9-phenyl] | $-C(CH_3)_3$ | $-CH_3$ | IR: 1720, 1670, 1490, 1430, 1300 cm$^{-1}$ |
| 106 | ![4-SC4H9-phenyl] | $-C(CH_3)_3$ | $-C_2H_5$ | IR: 1720, 1665, 1490, 1420, 1280 cm$^{-1}$ |
| 107 | ![4-SC4H9-phenyl] | $-C(CH_3)_3$ | $-C_3H_7$ | IR: 1720, 1670, 1490, 1420, 1280 cm$^{-1}$ |
| 108 | ![4-SC4H9-phenyl] | $-C(CH_3)_3$ | $-CH_2CH=CH_2$ | IR: 1720, 1670, 1495, 1420, 1280 cm$^{-1}$ |

-continued

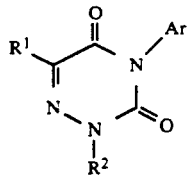
(I)

| Example No. | Ar | R¹ | R² | Physical constants |
|---|---|---|---|---|
| 109 | 4-$OC_4H_9$-C₆H₄- | $-C(CH_3)_3$ | $-C_3H_7$ | IR: 1720, 1670, 1420, 1250 cm$^{-1}$ |
| 110 | 4-$OC_4H_9$-C₆H₄- | $-C(CH_3)_3$ | $-C_2H_5$ | IR: 1720, 1660, 1240 cm$^{-1}$ |
| 111 | 4-$C(CH_3)_3$-C₆H₄- | $-CH_2-CH(CH_3)_2$ | $-CH_3$ | M.p. = 106° C. |
| 112 | 4-$C(CH_3)_3$-C₆H₄- | $-C_3H_7$ | $-CH_2-CH(CH_3)_2$ | IR: 1720, 1670, 1430, 1285 cm$^{-1}$ |
| 113 | 4-$CH(CH_3)_2$-C₆H₄- | $-C(CH_3)_2CH_2F$ | $-CH_2CH=CH_2$ | IR: 1720, 1675, 1420, 1280 cm$^{-1}$ |
| 114 | 4-$CH(CH_3)_2$-C₆H₄- | $-C(CH_3)_2CH(CH_3)_2$ | $-CH_3$ | IR: 1720, 1670, 1430, 1300 cm$^{-1}$ |
| 115 | 4-$CH(CH_3)_2$-C₆H₄- | $-C(CH_3)_2CH(CH_3)_2$ | $-C_2H_5$ | IR: 1720, 1660, 1280 cm$^{-1}$ |
| 116 | 4-$CH(CH_3)_2$-C₆H₄- | $-C(CH_3)_2CH(CH_3)_2$ | $-C_3H_7$ | IR: 1720, 1670, 1420, 1280 cm$^{-1}$ |
| 117 | 4-$CH(CH_3)_2$-C₆H₄- | $-C(CH_3)_2CH(CH_3)_2$ | $-CH_2CH=CH_2$ | IR: 1720, 1670, 1410, 1270 cm$^{-1}$ |
| 118 | 4-$CH(CH_3)_2$-C₆H₄- | $-C(CH_3)(C_2H_5)(C_4H_9)$ | $-C_2H_5$ | IR: 1720, 1670, 1420, 1285 cm$^{-1}$ |
| 119 | 4-$CH(CH_3)_2$-C₆H₄- | $-C(CH_3)(C_2H_5)(C_4H_9)$ | $-CH_2CH=CH_2$ | |

-continued

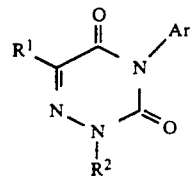
(I)

| Example No. | Ar | R¹ | R² | Physical constants |
|---|---|---|---|---|
| 120 | 4-C(CH₃)₃-C₆H₄- | -C(CH₃)₂CH(CH₃)₂ | -C₂H₅ | IR: 1720, 1670, 1420, 1280, 760 cm⁻¹ |
| 121 | 4-C(CH₃)₃-C₆H₄- | -C(CH₃)(C₂H₅)(C₄H₉) | -C₂H₅ | IR: 1720, 1665, 1415, 1280 cm⁻¹ |
| 122 | 4-C(CH₃)₃-C₆H₄- | -C(CH₃)(C₂H₅)(C₄H₉) | -CH₂CH=CH₂ | IR: 1720, 1670, 1410, 1270 cm⁻¹ |
| 123 | 4-C(CH₃)₃-C₆H₄- | -C(CH₃)₂CH(CH₃)₂ | -CH₂CH=CH₃ | IR: 1720, 1660, 1410, 1270, 750 cm⁻¹ |
| 124 | 4-C(CH₃)₃-C₆H₄- | -C(CH₃)₂CH(CH₃)₂ | -CH₂C≡CH | IR: 1720, 1670, 1420, 1275 cm⁻¹ |
| 125 | 4-C(CH₃)₃-C₆H₄- | -C(CH₃)₂CH₂F | -C₂H₅ | IR: 1720, 1670, 1420, 1285, 1050 cm⁻¹ (CHCl₃-Lösung) |
| 126 | 4-CH(CH₃)₂-C₆H₄- | -C(CH₃)₂CH₂-O-C₂H₅ | -C₂H₅ | M.p. = 80° C. |
| 127 | 4-CH(CH₃)₂-C₆H₄- | -C(CH₃)₂CH₂-O-C₂H₅ | -CH₂CH=CH₂ | IR: 1720, 1670, 1410, 1105 cm⁻¹ |
| 128 | 4-C₂H₅-C₆H₄- | -C(CH₃)₃ | -C₂H₅ | M.p. = 90° C. |
| 129 | 4-C₂H₅-C₆H₄- | -C(CH₃)₃ | -C₃H₇ | M.p. = 90° C. |
| 130 | 4-C₂H₅-C₆H₄- | -C(CH₃)₃ | -CH₂CH=CH₂ | M.p. = 82° C. |
| 131 | 4-C₄H₉-C₆H₄- | -C(CH₃)₃ | -C₂H₅ | M.p. = 58° C. |

-continued

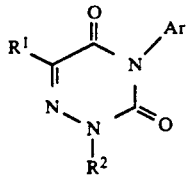
(I)

| Example No. | Ar | R¹ | R² | Physical constants |
|---|---|---|---|---|
| 132 | 4-C₄H₉-C₆H₄- | —C(CH₃)₃ | —C₃H₇ | M.p. = 60° C. |
| 133 | 4-C₄H₉-C₆H₄- | —C(CH₃)₃ | —CH₂CH=CH₂ | M.p. = 74° C. |
| 134 | 4-C₄H₉-C₆H₄- | —C(CH₃)₃ | —CH₂—CH(CH₃)₂ | M.p. = 60° C. |
| 135 | 4-C₄H₉-C₆H₄- | —C(CH₃)₃ | —CH₂—CH=CHCH₃ | IR: 1720, 1665, 1420, 1275 cm⁻¹ |
| 136 | 4-CH(CH₃)(C₂H₅)-C₆H₄- | —C(CH₃)₃ | —CH₃ | IR: 1720, 1675, 1425, 1300 cm⁻¹ |
| 137 | 4-CH(CH₃)(C₂H₅)-C₆H₄- | —C(CH₃)₃ | —C₃H₇ | IR: 1710, 1660, 1410, 1280 cm⁻¹ |
| 138 | 4-CH(CH₃)(C₂H₅)-C₆H₄- | —C(CH₃)₃ | —CH₂CH=CH₂ | IR: 1720, 1675, 1420, 1280 cm⁻¹ |
| 139 | 4-CH(CH₃)(C₂H₅)-C₆H₄- | —C(CH₃)₃ | —C₂H₅ | IR: 1720, 1670, 1420, 1280 cm⁻¹ |
| 140 | 4-O—CH(CH₃)[C(CH₃)₃]-C₆H₄- | —C(CH₃)₃ | —CH₃ | |
| 141 | 4-OCH(CH₃)[C(CH₃)₃]-C₆H₄- | —C(CH₃)₃ | —C₃H₇ | IR: 1720, 1670, 1250 cm⁻¹ |
| 142 | 4-OCH(CH₃)[C(CH₃)₃]-C₆H₄- | —C(CH₃)₃ | —C₂H₅ | IR: 1720, 1660–1680 1250 cm⁻¹ |

-continued

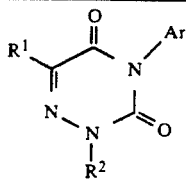

| Example No. | Ar | $R^1$ | $R^2$ | Physical constants |
|---|---|---|---|---|
| 143 | ⌬—OCH(CH₃)[C(CH₃)₃] (should be $-C_6H_4-OCH(CH_3)[C(CH_3)_3]$) | $-C(CH_3)_3$ | $-CH_2CH=CH_2$ | M.p. = 104° C. |
| 144 | $-C_6H_4-OCH(CH_3)[C(CH_3)_3]$ | $-C(CH_3)_3$ | $-CH_2C\equiv CH$ | |
| 145 | $-C_6H_4-OCH(CH_2F)_2$ | $-C(CH_3)_3$ | $-C_2H_5$ | M.p. = 102° C. |
| 146 | $-C_6H_4-N(C_4H_9)_2$ | $-C(CH_3)_3$ | $-CH_3$ | IR: 1718, 1670, 1295, 750 cm$^{-1}$ |
| 147 | $-C_6H_4-OCH(CH_2F)_2$ | $-C(CH_3)_3$ | $-CH_2CH=CH_2$ | IR: 1715, 1660, 1240 cm$^{-1}$ |
| 148 | $-C_6H_4-N(C_4H_9)_2$ | $-C(CH_3)_3$ | $-C_2H_5$ | IR: 1710, 1660, 1280, 750 cm$^{-1}$ |
| 149 | $-C_6H_4-N(C_3H_7)_2$ | $-C(CH_3)_3$ | $-CH_2CH=CH_2$ | IR: 1715, 1670, 1520 1400, 1120 cm$^{-1}$ |
| 150 | $-C_6H_4-N(C_3H_7)_2$ | $-C(CH_3)_3$ | $-C_2H_5$ | IR: 1710, 1665, 1510 cm$^{-1}$ | br* means "broad", wide band

PREPARATION EXAMPLES OF THE FORMULA (II)

(Example No. II-2)

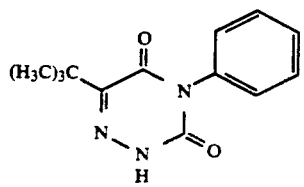

10 g (0.038 mol) of 4-phenyl-6-tert.-butyl-3-thioxo-1,2,4-triazin-5-one are dissolved in a solution of 6.43 g (0.115 mol) of potassium hydroxide in 170 ml of methanol/water=2:1 and a solution of 12 ml of hydrogen peroxide in 50 ml of water is added. The mixture is subsequently stirred at room temperature for 35 minutes and then acidified with a solution of 11 ml of conc. hydrochloric acid in 50 ml of water. The reaction product which precipitates is filtered off with suction, washed with water and dried. 9.0 g (85% of theory) of desired substance are obtained. For physical data see Example No. II-2 in the following table.

The compounds of the formula (II) mentioned in the following table are prepared analogously to the example given or to the methods described in the text.

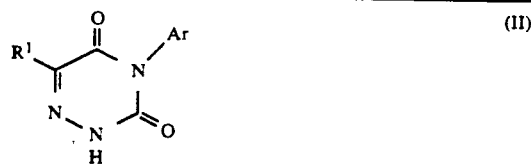
(II)
| Example No. | Ar | R¹ | Physical constants |
|---|---|---|---|
| II-1 | 4-OCF₃-C₆H₄ | —C(CH₃)₃ | M.p. = 128° C. |
| II-2 | C₆H₅ | —C(CH₃)₃ | M.p. = 192° C. |
| II-3 | 4-Cl-C₆H₄ | —C(CH₃)₃ | IR: 1722, 1675 cm⁻¹ |
| II-4 | 4-OCH₃-C₆H₄ | —C(CH₃)₃ | M.p. = 194° C. |
| II-5 | 4-CH₃-C₆H₄ | —C(CH₃)₃ | IR: 1720, 1670 cm⁻¹ |
| II-6 | 2-OCH₃-C₆H₄ | —C(CH₃)₃ | M.p. = 210° C. |
| II-7 | 4-OC₂H₅-C₆H₄ | —C(CH₃)₃ | IR: 1720, 1670 cm⁻¹ |
| II-8 | 2-Cl-C₆H₄ | —C(CH₃)₃ | M.p. = 214° C. |
| II-9 | 3,5-(CH₃)₂-C₆H₃ | —C(CH₃)₃ | M.p. = 186° C. |
| II-10 | 4-C(CH₃)₃-C₆H₄ | —C(CH₃)₃ | M.p. = 198° C. |

-continued
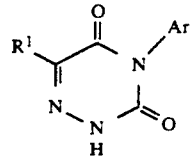
(II)
| Example No. | Ar | R¹ | Physical constants |
|---|---|---|---|
| II-11 | 2,4,5-tri(CH₃)-C₆H₂ | —C(CH₃)₃ | M.p. = 260° C. |
| II-12 | 2,6-di(CH₃)-C₆H₃ | —C(CH₃)₃ | M.p. = 260° C. |
| II-13 | 2,5-di(CH₃)-C₆H₃ | —C(CH₃)₃ | M.p. = 252° C. |
| II-14 | 4-CH(CH₃)₂-C₆H₄ | —C(CH₃)₃ | M.p. = 182° C. |
| II-15 | 2,6-di(Cl)-C₆H₃ | —C(CH₃)₃ | M.p. = 260° C. |
| II-16 | 3,5-di(Cl)-C₆H₃ | —C(CH₃)₃ | M.p. = 251° C. |
| II-17 | 2,3-di(Cl)-C₆H₃ | —C(CH₃)₃ | M.p. = 188° C. |
| II-18 | 2,4-di(Cl)-C₆H₃ | —C(CH₃)₃ | M.p. = 190° C. |
| II-19 | 4-CH(CH₃)₂-C₆H₄ | —CH(CH₃)₂ | M.p. = 160° C. |

-continued
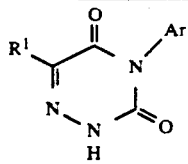
(II)
| Example No. | Ar | R¹ | Physical constants |
|---|---|---|---|
| II-20 | 4-C(CH₃)₃-C₆H₄- | —CH(CH₃)₂ | M.p. = 170° C. |
| II-21 | 4-OCF₃-C₆H₄- | —CH(CH₃)₂ | M.p. = 150° C. |
| II-22 | 4-N(CH₃)₂-C₆H₄- | —CH(CH₃)₂ | M.p. = 220° C. |
| II-23 | 2-Cl-C₆H₄- | —CH(CH₃)₂ | M.p. = 142° C. |
| II-24 | 4-OC₂H₅-C₆H₄- | —CH(CH₃)₂ | M.p. = 150° C. |
| II-25 | 4-cyclohexyl-C₆H₄- | —CH(CH₃)₂ | M.p. = 178° C. |
| II-26 | 2-OCH₃-C₆H₄- | —CH(CH₃)₂ | M.p. = 166° C. |
| II-27 | 4-CH₃-C₆H₄- | —CH(CH₃)₂ | M.p. = 184° C. |
| II-28 | 4-(CH₂)₅CH₃-C₆H₄- | —C(CH₃)₃ | M.p. = 114° C. |
| II-29 | 4-cyclohexyl-C₆H₄- | —C(CH₃)₃ | M.p. = 186° C. |
| II-30 | 2,4,6-(CH₃)₃-C₆H₂- | —CH₃ | IR: 1722, 1660 cm⁻¹ |

-continued (II)

structure: R¹ group at 5-position, N-Ar at 4-position, with 1,2,4-triazine-3,5(2H,4H)-dione core (NH at N-2)

| Example No. | Ar | R¹ | Physical constants |
|---|---|---|---|
| II-31 | 4-CH(CH₃)₂-C₆H₄- | —C(CH₃)(C₂H₅)₂ | M.p. = 172° C. |
| II-32 | 4-CH(C₂H₅)₂-C₆H₄- | —C(CH₃)₃ | M.p. = 136° C. |
| II-33 | 4-[CH(CH₃)CH(CH₃)₂]-C₆H₄- | —C(CH₃)₃ | M.p. = 184° C. |
| II-34 | 4-N(CH₃)₂-C₆H₄- | —C(CH₃)₃ | M.p. = 238° C. |
| II-35 | 4-C₃H₇-C₆H₄- | —C(CH₃)₃ | M.p. = 220° C. |
| II-36 | 4-N(C₂H₅)₂-C₆H₄- | —C(CH₃)₃ | M.p. = 240° C. |
| II-37 | 4-C(CH₃)₃-C₆H₄- | —C(CH₃)(C₂H₅)₂ | M.p. = 206° C. |
| II-38 | 4-SC₄H₉-C₆H₄- | —C(CH₃)₃ | IR: 1720, 1660 cm⁻¹ |
| II-39 | 4-OC₄H₉-C₆H₄- | —C(CH₃)₃ | IR: 1720, 1665, 1250 cm⁻¹ |
| II-40 | 4-C(CH₃)₃-C₆H₄- | —C(CH₃)(C₂H₅)(C₄H₉) | IR: 1725, 1670, 760 cm⁻¹ |
| II-41 | 4-CH(CH₃)₂-C₆H₄- | —C(CH₃)(C₂H₅)(C₄H₉) | IR: 1720, 1660, 1420, 1230 cm⁻¹ |
| II-42 | 4-C(CH₃)₃-C₆H₄- | —C(CH₃)₂CH(CH₃)₂ | IR: 1725, 1670, 1425 cm⁻¹ |

-continued

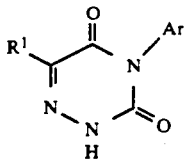

(II)

| Example No. | Ar | $R^1$ | Physical constants |
|---|---|---|---|
| II-43 | 4-CH(CH$_3$)$_2$-C$_6$H$_4$- | —C(CH$_3$)$_2$CH(CH$_3$)$_2$ | IR: 1730, 1670, 1420 cm$^{-1}$ |
| II-44 | 4-C(CH$_3$)$_3$-C$_6$H$_4$- | —C(CH$_3$)$_2$CH$_2$F | M.p. = 178° C. |
| II-45 | 4-CH(CH$_3$)$_2$-C$_6$H$_4$- | —C(CH$_3$)$_2$CH$_2$—OC$_2$H$_5$ | M.p. = 124° C. |
| II-46 | 4-C$_2$H$_5$-C$_6$H$_4$- | —C(CH$_3$)$_3$ | M.p. = 162° C. |
| II-47 | 4-C$_4$H$_9$-C$_6$H$_4$- | —C(CH$_3$)$_3$ | M.p. = 168° C. |
| II-48 | 4-CH(CH$_3$)(C$_2$H$_5$)-C$_6$H$_4$- | —C(CH$_3$)$_3$ | M.p. = 156° C. |
| II-49 | 4-OCH(CH$_2$F)$_2$-C$_6$H$_4$- | —C(CH$_3$)$_3$ | M.p. = 164° C. |
| II-50 | 4-N(C$_4$H$_9$)$_2$-C$_6$H$_4$- | —C(CH$_3$)$_3$ | IR: 1720, 1660, 750 cm$^{-1}$ |
| II-51 | 4-N(C$_3$H$_7$)$_2$-C$_6$H$_4$- | —C(CH$_3$)$_3$ | IR: 1730, 1670 cm$^{-1}$ |
| II-52 | 4-CH(CH$_3$)$_2$-C$_6$H$_4$- | —C$_2$H$_5$ | M.p. = 200° C. |

PREPARATION EXAMPLES OF THE COMPOUNDS OF THE FORMULA (IV)

(Example No. IV-2)

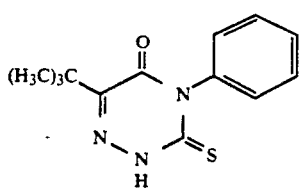

33.4 g (0.2 mol) of 4-phenyl-thiosemicarbazide and 30.4 g (0.2 mol) of 2-keto-3,3-dimethylbutyric acid Na salt are boiled under reflux for 8 hours in a solution of 55 ml of conc. hydrochloric acid in 1 l of water. After cooling, the reaction product is filtered off with suction, washed with plenty of water and dried. 39.5 g (76% of theory) of desired product are obtained. For physical data see Example IV-2 in the following table.

The compounds of the formula (IV) mentioned in the following table are prepared analogously to the example given:

(IV)

| Example No. | Ar | $R^1$ | Physical constants |
|---|---|---|---|
| IV-1 | —⟨⟩—OCF₃ | —C(CH₃)₃ | M.p. = 186° C. |
| IV-2 | —⟨⟩ | —C(CH₃)₃ | M.p. = 222° C. |
| IV-3 | —⟨⟩—Cl | —C(CH₃)₃ | M.p. = 186° C. |
| IV-4 | —⟨⟩—OCH₃ | —C(CH₃)₃ | M.p. = 214° C. |
| IV-5 | —⟨⟩—CH₃ | —C(CH₃)₃ | M.p. = 196° C. |
| IV-6 | —⟨⟩ (o-OCH₃) | —C(CH₃)₃ | M.p. = 220° C. |
| IV-7 | —⟨⟩—OC₂H₅ | —C(CH₃)₃ | M.p. = 196° C. |
| IV-8 | —⟨⟩ (o-Cl) | —C(CH₃)₃ | M.p. = 200° C. |

-continued
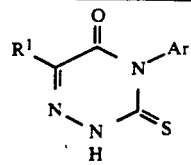
(IV)
| Example No. | Ar | R¹ | Physical constants |
|---|---|---|---|
| IV-9 | 2,5-dimethylphenyl | —C(CH$_3$)$_3$ | M.p. = 184° C. |
| IV-10 | 4-tert-butylphenyl | —C(CH$_3$)$_3$ | M.p. = 228° C. |
| IV-11 | 2,4,6-trimethylphenyl | —C(CH$_3$)$_3$ | M.p. = 260° C. |
| IV-12 | 2,6-dimethylphenyl | —C(CH$_3$)$_3$ | M.p. = 192° C. |
| IV-13 | 2,4-dimethylphenyl | —C(CH$_3$)$_3$ | M.p. = 208° C. |
| IV-14 | 4-isopropylphenyl | —C(CH$_3$)$_3$ | M.p. = 202° C. |
| IV-15 | 2,4-dichlorophenyl | —C(CH$_3$)$_3$ | M.p. = 216° C. |
| IV-16 | 2,3-dichlorophenyl | —C(CH$_3$)$_3$ | M.p. = 212° C. |
| IV-17 | 3,5-dichlorophenyl | —C(CH$_3$)$_3$ | M.p. = 188° C. |

-continued

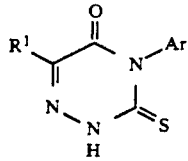
(IV)

| Example No. | Ar | R¹ | Physical constants |
|---|---|---|---|
| IV-18 | 2,6-dichlorophenyl | —C(CH$_3$)$_3$ | M.p. = 186° C. |
| IV-19 | phenyl | —CH(CH$_3$)$_2$ | M.p. = 196° C. |
| IV-20 | 4-isopropylphenyl | —CH(CH$_3$)$_2$ | M.p. = 180° C. |
| IV-21 | 4-tert-butylphenyl | —CH(CH$_3$)$_2$ | M.p. = 196° C. |
| IV-22 | 4-trifluoromethoxyphenyl | —CH(CH$_3$)$_2$ | M.p. = 152° C. |
| IV-23 | 4-(N,N-dimethylamino)phenyl | —CH(CH$_3$)$_2$ | M.p. = 212° C. |
| IV-24 | 4-cyclohexylphenyl | —CH(CH$_3$)$_2$ | M.p. = 218° C. |
| IV-25 | 2,4,6-trimethylphenyl | —CH$_3$ | M.p. = 230° C. (subl.) |
| IV-26 | 4-methylphenyl | —CH(CH$_3$)$_2$ | M.p. = 170° C. |
| IV-27 | 2-chlorophenyl | —CH(CH$_3$)$_2$ | M.p. = 154° C. |

-continued

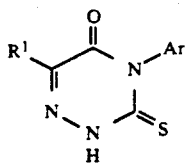
(IV)

| Example No. | Ar | R¹ | Physical constants |
|---|---|---|---|
| IV-28 | —⟨C₆H₄⟩—OC₂H₅ | —CH(CH₃)₂ | M.p. = 180° C. |
| IV-29 | —⟨C₆H₄⟩—C₆H₁₁ | —C(CH₃)₃ | M.p. = 189° C. |
| IV-30 | 2-H₃CO—⟨C₆H₄⟩— | —CH(CH₃)₂ | M.p. = 146° C. |
| IV-31 | —⟨C₆H₄⟩—(CH₂)₅CH₃ | —C(CH₃)₃ | M.p. = 182° C. |
| IV-32 | —⟨C₆H₄⟩—CH(CH₃)₂ | —C(CH₃)(C₂H₅)₂ | M.p. = 154° C. |
| IV-33 | —⟨C₆H₄⟩—CH(CH₃)—CH(CH₃)₂ | —C(CH₃)₃ | M.p. = 162° C. |
| IV-34 | —⟨C₆H₄⟩—CH(C₂H₅)₂ | —C(CH₃)₃ | M.p. = 182° C. |
| IV-35 | —⟨C₆H₄⟩—C(CH₃)₃ | —C(CH₃)(C₂H₅)₂ | M.p. = 166° C. |
| IV-36 | —⟨C₆H₄⟩—N(CH₃)₂ | —C(CH₃)₃ | M.p. = 210° C. |
| IV-37 | —⟨C₆H₄⟩—N(C₂H₅)₂ | —C(CH₃)₃ | M.p. = 250° C. |
| IV-38 | —⟨C₆H₄⟩—C₃H₇ | —C(CH₃)₃ | M.p. = 233° C. |

-continued

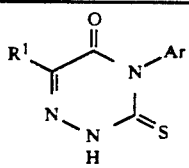
(IV)

| Example No. | Ar | R¹ | Physical constants |
|---|---|---|---|
| IV-39 | —⟨C₆H₄⟩—SC₄H₉ | —C(CH₃)₃ | IR: 1680–1710 cm⁻¹ |
| IV-40 | —⟨C₆H₄⟩—OC₄H₉ | —C(CH₃)₃ | IR: 1700 cm⁻¹ |
| IV-41 | —⟨C₆H₄⟩—C(CH₃)₃ | —C(CH₃)(C₂H₅)(C₄H₉) | IR: 1700, 1260 cm⁻¹ |
| IV-42 | —⟨C₆H₄⟩—CH(CH₃)₂ | —C(CH₃)(C₂H₅)(C₄H₉) | IR: 1700, 1255 cm⁻¹ |
| IV-43 | —⟨C₆H₄⟩—C(CH₃)₃ | —C(CH₃)₂CH(CH₃)₂ | IR: 1700, 1260 cm⁻¹ |
| IV-44 | —⟨C₆H₄⟩—CH(CH₃)₂ | —C(CH₃)₂CH(CH₃)₂ | IR: 1700, 1260 cm⁻¹ |
| IV-45 | —⟨C₆H₄⟩—C(CH₃)₃ | —C(CH₃)₂—CH₂F | M.p. = 224° C. |
| IV-46 | —⟨C₆H₄⟩—CH(CH₃)₂ | —C(CH₃)₂—CH₂OC₂H₅ | M.p. = 122° C. |
| IV-47 | —⟨C₆H₄⟩—C₂H₅ | —C(CH₃)₃ | IR: 1705, 1270 cm⁻¹ |
| IV-48 | —⟨C₆H₄⟩—C₄H₉ | —C(CH₃)₃ | IR: 1690–1720 cm⁻¹ |
| IV-49 | —⟨C₆H₄⟩—CH(CH₃)(C₂H₅) | —C(CH₃)₃ | M.p. = 180° C. |
| IV-50 | —⟨C₆H₄⟩—OCH(CH₂F)₂ | —C(CH₃)₃ | IR: 1700, 1500, 1280, 1250 cm⁻¹ |

-continued

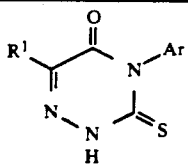

| Example No. | Ar | R¹ | Physical constants |
|---|---|---|---|
| IV-51 | —⟨phenyl⟩—N(C₄H₉)₂ | —C(CH₃)₃ | M.p. = 179° C. |
| IV-52 | —⟨phenyl⟩—N(C₃H₇)₂ | —C(CH₃)₃ | M.p. = 177° C. |
| IV-53 | —⟨phenyl⟩—CH(CH₃)₂ | —C₂H₅ | M.p. = 186° C. |

USE EXAMPLES

The following compound was used as a comparison substance:

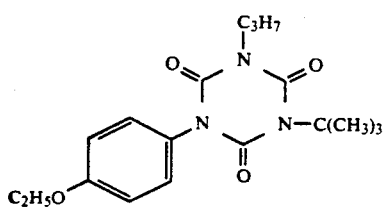

Example A

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

It will be appreciated that the instant specification is set forth by way of illustration and not limitation, and that various modifications and changes may be made without departing from the spirit and scope of the present invention.

What is claimed is:

1. A trisubstituted 1,2,4-triazine-3,5-dione of the formula

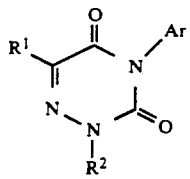

in which

Ar represents phenyl which is optionally monosubstituted to pentasubstituted by identical or different substituents from the group consisting of halogen, alkyl having 1 to 10 carbon atoms, alkenyl having 2 to 10 carbon atoms, alkynyl having 2 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino with straight-chain or branched alkyl radicals having 1 to 6 carbon atoms, dialkylamino with identical or different, straight-chain or branched alkyl radicals each having 1 to 6 carbon atoms, cycloalkyl or cycloalkenyl having 3 to 8 carbon atoms which are optionally monosubstituted to hexasubstituted by identical or different substituents from the group consisting of halogen, alkyl having 1 to 4 carbon atoms, alkoxy having 1 to 4 carbon atoms, halogenoalkyl having 1 to 4 carbon atoms or halogenoalkoxy having 1 to 4 carbon atoms and in each case 1 to 9 identical or different halogen atoms, alkylthio having 1 to 4 carbon atoms and halogenoalkylthio having 1 to 4 carbon atoms and 1 to 5 identical or different halogen atoms, R¹ represents straight-chain or branched alkyl having 1 to 12 carbon atoms, straight-chain or branched alkenyl having 3 to 12 carbon atoms or straight-chain or branched alkinyl having 3 to 12 carbon atoms, which are optionally monosubstituted to polysubstituted by identical or different substituents from the group consisting of halogen, alkoxy having 1 to 4 carbon atoms, halogenoalkoxy having 1 to 4 carbon atoms and 1 to 9 identical or different halogen atoms, alkylthio having 1 to 4 carbon atoms and halogenoalkylthio having 1 to 4 carbon atoms and 1 to 9 identical or different halogen atoms; or R¹ represents cycloalkyl having 3 to 8 carbon atoms, which is optionally monosubstituted to hexasubstituted by identical or different substituents from the group consisting of halogen, alkyl having 1 to 4 carbon atoms, alkoxy having 1 to 4 carbon atoms, halogenoalkyl or halogenoalkoxy having 1 to 4 carbon atoms and 1 to 9 identical or different halogen atoms, alkylthio having 1 to 4 carbon atoms and halogenoalkylthio having 1 to 4 carbon atoms and 1 to 9 identical or different halogen atoms, R² represents alkyl having 1 to 10 carbon atoms, alkenyl having 3 to 10 carbon atoms, alkynyl having 3 to 10 carbon atoms, alkoxyalkyl in each case having 1 to 4 carbon atoms in the alkoxy and in the alkyl moiety, alkylthioalkyl in each case having 1 to 4 carbon atoms in the alkylthio moiety and in the alkyl moiety, alkoxycarbonylalkyl having 1 to 4 carbon atoms in the alkoxy moiety and 1 to 3 carbon atoms in the alkyl moiety or represents cyanoalkyl having 1 to 5 carbon atoms in the alkyl moiety.

2. A trisubstituted 1,2,4-triazine-3,5-dione according to claim 1 in which

Ar represents phenyl which is optionally monosubstituted to tetrasubstituted by identical or different substituents from the group consisting of fluorine, chlorine, bromine, alkyl having 1 to 9 carbon atoms, alkenyl having 2 to 9 carbon atoms, alkynyl having 2 to 9 carbon atoms, halogenoalkyl having 1 to 7 carbon atoms and 1 to 7 chlorine plus fluorine atoms, alkoxy having 1 to 9 carbon atoms, halogenoalkoxy having 1 to 7 carbon atoms and 1 to chlorine plus fluorine atoms, alkylthio having to 9 carbon atoms, halogenoalkylthio having 1 to carbon atoms and 1 to 7 chlorine plus fluorine atoms, amino, monoalkylamino with a straight-chain or branched alkyl radical having 1 to 5 carbon atoms, dialkylamino with identical or different straight-chain or branched alkyl radicals each having 1 to 5 carbon atoms cycloalkyl or cycloalkenyl having 3 to 7 carbon atoms, which is optionally monosubstituted to pentasubstituted by identical or different substituents from the group consisting of chlorine, fluorine, alkyl having 1 to 3 carbon atoms, alkoxy having 1 to 3 carbon atoms, halogenoalkoxy having 1 to 3 carbon atoms and 1 to 5 chlorine plus fluorine atoms, alkylthio having 1 to 3 carbon atoms and halogenoalkylthio having 1 to 3 carbon atoms and 1 to 5 chlorine plus fluorine atoms, R¹ represents straight-chain or branched alkyl having 1 to 10 carbon atoms, straight-chain or branched alkenyl having 3 to 10 carbon atoms, or straight-chain or branched alkynyl having 3 to 10 carbon atoms, which are in each case optionally monosubstituted to trisubstituted by identical or different substituents from the group consisting of chlorine, fluorine, alkoxy having 1 to 3 carbon atoms, halogenoalkoxy having 1 to 3 carbon atoms and 1 to 3 chlorine plus fluorine atoms, alkylthio having 1 to 3 carbon atoms and halogenoalkylthio having 1 to 3 carbon atoms and 1 to 3 chlorine plus fluorine atoms; or R¹ furthermore represents cycloalkyl having 3 to 7 carbon atoms which is optionally monosubstituted to hexasubstituted by identical or different substituents from the group consisting of fluorine, chlorine, alkyl having 1 to 3 carbon atoms, alkoxy having 1 to 3 carbon atoms, halogenoalkoxy having 1 to 3 carbon atoms and 1 to 3 chlorine alkynyl fluorine atoms, alkylthio having 1 to 3 carbon atoms and halogenoalkylthio having 1 to 3 carbon atoms and 1 to 3 chlorine plus fluorine atoms, R² represents alkyl having 1 to 9 carbon atoms, alkenyl having 3 to 9 carbon atoms, alkynyl having 3 to 9 carbon atoms, alkoxyalkyl having 1 or 2 carbon atoms in the alkoxy moiety and 1 to 3 carbon atoms in the alkyl moiety, alkylthioalkyl having 1 or 2 carbon atoms in the alkylthio moiety and 1 to 3 carbon atoms in the alkyl moiety, alkoxycarbonylalkyl having 1 or 2 carbon atoms in the alkoxy moiety and 2 or 3 carbon atoms in the alkyl moiety, or cyanoalkyl having 1 to 3 carbon atoms in the alkyl moiety.

3. A trisubstituted 1,2,4-triazine-3,5-dione according to claim 1 in which

Ar represents phenyl which is optionally monosubstituted to trisubstituted by identical or different substituents from the group consisting of fluorine, chlorine, bromine, alkyl having 1 to 8 carbon atoms, alkenyl having 2 to 8 carbon atoms, alkynyl having 2 to 8 carbon atoms, halogenoalkyl having 1 to 6 carbon atoms and 1 to 5 chlorine plus fluorine atoms, alkoxy having 1 to 8 carbon atoms, halogenoalkoxy having 1 to 6 carbon atoms and 1 to 5 chlorine plus fluorine atoms, alkylthio having 1 to 8 carbon atoms, halogenoalkylthio having 1 to 6 carbon atoms and 1 to 5 chlorine plus fluorine atoms, amino, monoalkylamino with a straight-chain or branched alkyl radical having 1 to 4 carbon atoms, dialkylamino with identical or different straight-chain or branched alkyl radicals each having 1 to 4 carbon atoms, cycloalkyl or cycloalkenyl having 3 to 6 carbon atoms which are optionally monosubstituted to tetrasubstituted by identical or different substituents from the group consisting of chlorine, fluorine, alkyl having 1 to 3 carbon atoms, alkoxy having 1 to 3 carbon atoms, halogenoalkoxy having 1 or 2 carbon atoms and 1 to 5 chlorine plus fluorine atoms, alkylthio having 1 or 2 carbon atoms and halogenoalkylthio having 1 or 2 carbon atoms and 1 to 5 chlorine plus fluorine atoms, R¹ represents straight-chain or branched alkyl having 1 to 9 carbon atoms, straight-chain or branched alkenyl having 3 to 9 carbon atoms or straight-chain or branched alkynyl having 3 to 9 carbon atoms, which in each case are optionally monosubstituted or disubstituted by identical or different substituents from the group consisting of chlorine, fluorine, alkoxy having 1 to 3 carbon atoms, halogenoalkoxy having 1 to 3 carbon atoms and 1 to 3 chlorine plus fluorine atoms, alkylthio having 1 to 3 carbon atoms and halogenoalkylthio having 1 to 3 carbon atoms and 1 to 3 chlorine plus fluorine atoms; or $R^1$ furthermore represents cycloalkyl having 3 to 7 carbon atoms which is optionally monosubstituted to pentasubstituted by identical or different substituents from the group consisting of fluorine, chlorine, alkyl having 1 or 2 carbon atoms, alkoxy having 1 or 2 carbon atoms, halogenoalkoxy having 1 or 2 carbon atoms and 1 to 4 chlorine plus fluorine atoms, alkylthio having 1 or 2 carbon atoms and halogenoalkylthio having 1 or 2 carbon atoms and 1 to 3 chlorine plus fluorine atoms, $R^2$ represents alkyl having 1 to 8 carbon atoms, alkenyl having 3 to 8 carbon atoms, alkynyl having 3 to 8 carbon atoms, alkoxyalkyl having 1 or 2 carbon atoms in the alkoxy moiety and 1 to 3 carbon atoms in the alkyl moiety, alkylthioalkyl having 1 or 2 carbon atoms in the alkylthio moiety and 1 to 3 carbon atoms in the alkyl moiety, alkoxycarbonylalkyl having 1 or 2 carbon atoms in the alkoxy moiety and 2 or 3 carbon atoms in the alkyl moiety or cyanoalkyl having 1 to 3 carbon atoms in the alkyl moiety.

4. A compound according to claim 1, wherein such compound is 2-methyl-4-(4-isopropyl-phenyl)-6-tert.-butyl-1,2,4-triazine-3,5-dione of the formula

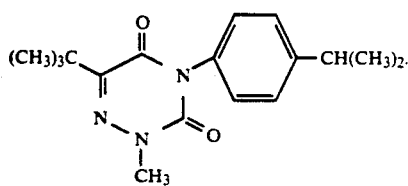

5. A compound according to claim 1, wherein such compound is 2-ethyl-4-(4-isopropyl-phenyl)-6-tert.-butyl-1,2,4-triazine-3,5-dione of the formula

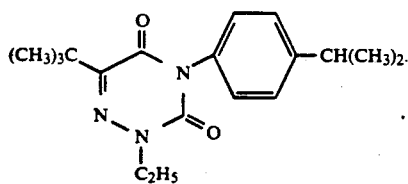

6. A compound according to claim 1, wherein such compound is 2-allyl-4-(4-isopropyl-phenyl)-6-tert.-butyl-1,2,4-triazine-3,5-dione of the formula

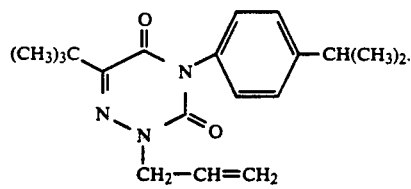

7. A fungicidal composition comprising a fungicidally effective amount of a compound according to claim 1 and a diluent.

8. A method of combating fungi which comprises applying to such fungi or to a fungus habitat a fungicidally effective amount of a compound according to claim 1.

9. The method according to claim 8, wherein such compound is
2-methyl-4-(4-isopropyl-phenyl)-6-tert.-butyl-1,2,4-triazine-3,5-dione,
2-ethyl-4-(4-isopropyl-phenyl)-6-tert.-butyl-1,2,4-triazine-3,5-dione, or
2-allyl-4-(4-isopropyl-phenyl)-6-tert.-butyl-1,2,4-triazine-3,5-dione.

10. A disubstituted 1,2,4-triazine-3,5-dione of the formula

(IIa)

in which
wherein Ar and $R^1$ have the meaning given in claim 1, excluding the compounds in which Ar represents phenyl or 4-methylphenyl and $R^1$ simultaneously represents methyl.

11. A disubstituted 3-thioxo-1,2,4-triazin-5-one of the formula

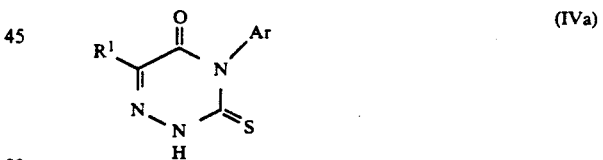

(IVa)

in which
wherein Ar and $R^1$ have the meaning given in claim 1, excluding the compounds in which Ar represents phenyl, 4-methylphenyl, 3-methylphenyl, 2-methoxyphenyl, 3-methoxyphenyl, 2-ethoxyphenyl or 4-chlorophenyl and $R^1$ simultaneously represents methyl.

* * * * *

UNITED STATES PATENT AND TRADEMARK OFFICE
CERTIFICATE OF CORRECTION

PATENT NO. : 5,096,903

DATED : March 17, 1992

INVENTOR(S) : Uhr et al.

It is certified that error appears in the above-identified patent and that said Letters Patent is hereby corrected as shown below:

Col. 63, line 46  After " to " (first occurrence) insert -- 7 --, before " to " (second occurrence) insert -- 1 --

Col. 63, line 48  Before " carbon " insert -- 7 --

Signed and Sealed this

Second Day of November, 1993

Attest:

BRUCE LEHMAN

Attesting Officer   Commissioner of Patents and Trademarks